US00PP29421P2

(12) United States Plant Patent
Smit

(10) Patent No.: US PP29,421 P2
(45) Date of Patent: Jun. 19, 2018

(54) ***SENECIO* PLANT NAMED 'PURPLE CHAIN'**

(50) Latin Name: *Senecio herreanus*
Varietal Denomination: PURPLE CHAIN

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 31 days.

(21) Appl. No.: 15/530,124

(22) Filed: Dec. 5, 2016

(51) Int. Cl.
*A01H 5/02* (2018.01)

(52) U.S. Cl.
USPC ..... Plt./480

(58) Field of Classification Search
USPC ..... Plt./480
See application file for complete search history.

*Primary Examiner* — Keith O Robinson

(57) ABSTRACT

A new cultivar of *Senecio* plant named 'PURPLE CHAIN' that is characterized by purple stems and green succulent leaves that have an elongated cylindrical shape.

1 Drawing Sheet

Botanical classification: *Senecio herreanus*.
Variety denomination: 'PURPLE CHAIN'.

BACKGROUND OF THE INVENTION

The present invention relates to a new and distinct cultivar of *Senecio* plant botanically known as *Senecio herreanus* and hereinafter referred to by the cultivar name 'PURPLE CHAIN'.

'PURPLE CHAIN' originated from the crossing of the female or seed parent, an unnamed proprietary *Senecio herreanus* cultivar and the male or pollen parent, an unnamed proprietary *Senecio herreanus* cultivar. The crossing was conducted in 2013 in Sappemeer, Netherlands. The resulting seeds were subsequently planted and grown. The cultivar 'PURPLE CHAIN' was selected by the inventor in 2014 in a controlled environment as a single plant within the progeny of the stated cross in a cultivated area of Sappemeer, Netherlands.

Asexual reproduction of the new cultivar 'PURPLE CHAIN' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Senecio* cultivar 'PURPLE CHAIN'. These traits in combination distinguish 'PURPLE CHAIN' as a new and distinct cultivar apart from other existing varieties of *Senecio* known by the inventor.

1. *Senecio* 'PURPLE CHAIN' exhibits purple stems.
2. *Senecio* 'PURPLE CHAIN' exhibits green succulent leaves that have an elongated cylindrical shape.

*Senecio* 'PURPLE CHAIN' can be compared to plants of the *Senecio rowleyanus* species and to plants of the *Senecio radicans* species. 'PURPLE CHAIN' is distinguishable from plants of the *Senecio rowleyanus* species by the following characteristics:

1. *Senecio* 'PURPLE CHAIN' exhibits purple stems. In comparison, the stems of plants of the *Senecio rowleyanus* species are light green.
2. *Senecio* 'PURPLE CHAIN' exhibits leaves that have an elongated cylindrical shape. In comparison, the leaves of plants of the *Senecio rowleyanus* species are spherical in shape.

'PURPLE CHAIN' is distinguishable from plants of the *Senecio radicans* species by the following characteristics:

1. *Senecio* 'PURPLE CHAIN' exhibits purple stems. In comparison, the stems of plants of the *Senecio radicans* species are dark green.
2. *Senecio* 'PURPLE CHAIN' exhibits leaves that have an elongated cylindrical shape. In comparison, the leaves of plants of the *Senecio radicans* species are curved with a bannna-like shape.

'PURPLE CHAIN' is distinguishable from the female parent plant by the following characteristics:

1. *Senecio* 'PURPLE CHAIN' exhibits purple stems. In comparison, the stems of the female parent plant are lighter purple in color.

'PURPLE CHAIN' is distinguishable from the male parent plant by the following characteristics:

1. *Senecio* 'PURPLE CHAIN' exhibits purple stems. In comparison, the stems of the male parent plant are lighter purple in color.

BRIEF DESCRIPTION OF THE DRAWING

The accompanying photograph illustrates the distinguishing traits of *Senecio* 'PURPLE CHAIN'. The photograph shows an overall view of a 20 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Senecio* cultivar named 'PURPLE CHAIN'. Data was collected in Sappemeer, Netherlands from 20 week old plants grown in a glass greenhouse in 10.5 cm. diameter containers. The time of year was Summer and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'PURPLE CHAIN' has not been tested under all possible conditions and phenotypic differences may be observed with variations in environmental, climatic, and cultural conditions, however, without any variance in genotype.

Botanical classification: *Senecio herreanus* 'PURPLE CHAIN'.

Annual or perennial: Perennial.

Parentage: 'PURPLE CHAIN' resulted from the crossing of the female or seed parent, an unnamed proprietary *Senecio herreanus* cultivar and the male or pollen parent, an unnamed proprietary *Senecio herreanus* cultivar.

Plant type: Pot plant.

Plant shape: Prostrate.

Growth habit: Creeping.

Suitable container size: 7 cm. pots or larger.

Plant height: 5.5 cm.

Plant width: 23.4 cm.

Vigor: Moderate.

Growth rate: Moderate.

Low temperature tolerance: 0° Centigrade.

High temperature tolerance: 40° Centigrade.

Propagation: Leaf cuttings.

Time to initiate roots (summer): 14 days at 18 to 20° C.

Time to initiate roots (winter): 21 days at 18 to 20° C.

Time to produce a rooted cutting: Leaf cuttings are placed directly into growing container.

Crop time: Approximately 20 weeks in Sappemeer, Netherlands.

Root system: Dense and fine.

Root color: N155.

Plant fragrance: None.

Pinching: Not required.

Stem:

- *Branching habit.*—Main stems with lateral branches.
- *Basal branching.*—Yes.
- *Number of main stems per plant.*—Average 11.
- *Number of lateral branches per plant.*—Average 22.
- *Lateral branch dimensions.*—8.3 cm. in length and 0.2 cm. in width.
- *Internode length.*—0.5 cm.
- *Stem shape.*—Rounded.
- *Stem texture.*—Smooth.
- *Stem pubescence.*—Absent.
- *Stem angle.*—Average 80 degrees from vertical.
- *Stem strength.*—Strong.
- *Stem color* (*young*).—N79D.
- *Stem color* (*mature*).—N79B, older main stems N187C and 200C.
- *Internode color.*—N79B.

Foliage:

- *Leaf arrangement.*—Alternate.
- *Compound or single.*—Single.
- *Quantity of leaves per lateral branch.*—Average 8.
- *Leaf shape.*—Obovate.
- *Leaf aspect.*—Circular in diameter.
- *Leaf apex.*—Short apiculate.
- *Leaf base.*—Cuneate.
- *Leaf dimensions.*—1.8 cm. in length and 0.55 cm. in width.
- *Leaf thickness.*—0.55 cm.
- *Texture.*—Glabrous both surfaces, slightly velvety, succulent.
- *Pubescence.*—Absent.
- *Leaf luster.*—Matte both surfaces.
- *Leaf rugosity.*—Non-rugose.
- *Leaf margin.*—None, leaves circular in diameter.
- *Venation pattern.*—None visible.
- *Young leaf color* (*upper surface*).—137C, base 138B to 138C.
- *Young leaf color* (*lower surface*).—137C, base 138B to 138C.
- *Mature leaf color* (*upper surface*).—In between N189A and 202B.
- *Mature leaf color* (*lower surface*).—189A.

Petiole:

- *Petiole dimensions.*—0.5 cm. in length and 0.2 cm. in diameter.
- *Petiole texture.*—Glabrous.
- *Petiole luster.*—Slightly glossy.
- *Petiole pubescence.*—Absent.
- *Petiole strength.*—Moderate.
- *Petiole color* (*upper surface*).—187B.
- *Petiole color* (*lower surface*).—N79D.

Flower: 'PURPLE CHAIN' has not produced flowers to date.

Fruit and seed: 'PURPLE CHAIN' has not produced fruit or seed to date.

Disease and pest resistance: Disease and pest resistance has not been observed.

The invention claimed is:

1. A new and distinct variety of *Senecio* plant named 'PURPLE CHAIN' as described and illustrated.

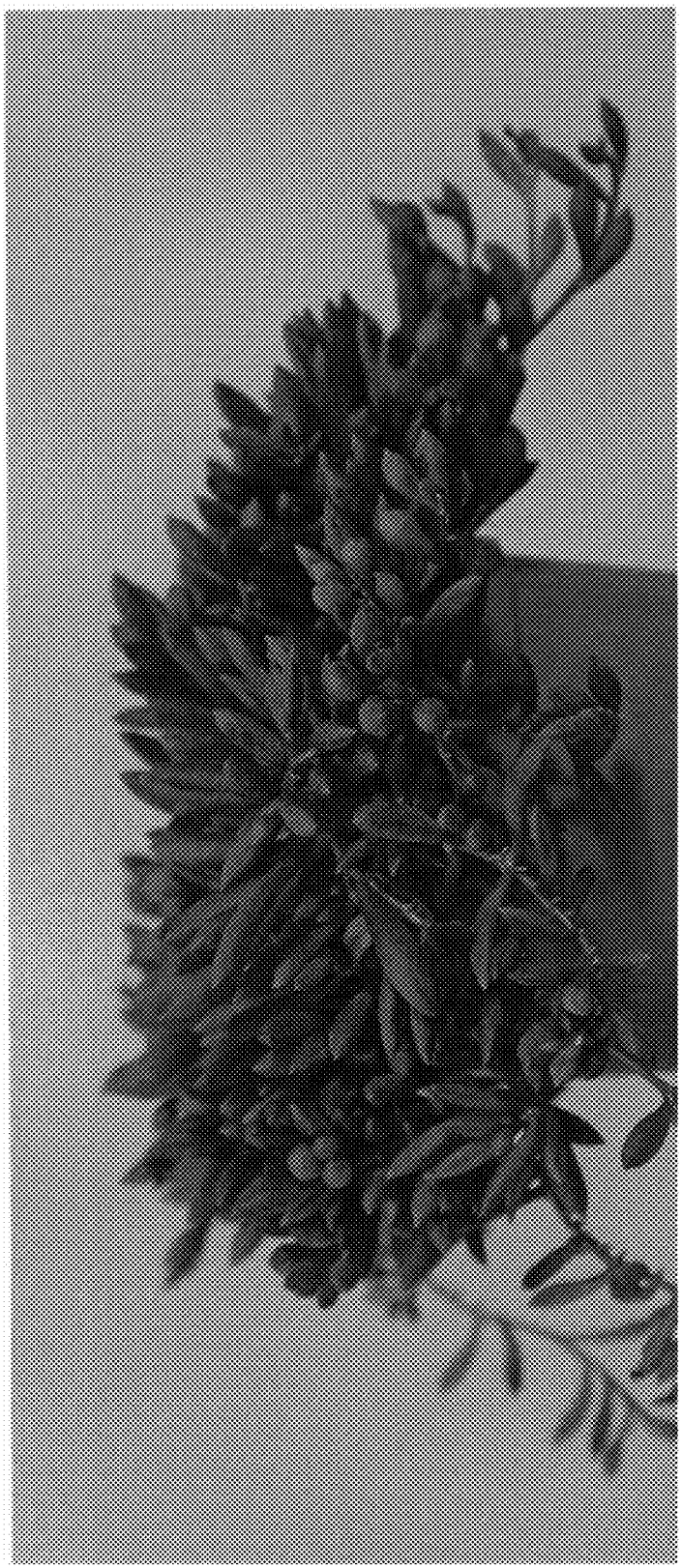

* * * * *